United States Patent [19]

Buser et al.

[11] Patent Number: 5,196,016
[45] Date of Patent: Mar. 23, 1993

[54] AUXILIARY MEANS AND METHOD FOR FASTENING A CAPPING ON BONE TISSUE OR THE LIKE

[75] Inventors: Daniel Buser, Muri bei Bern; Franz Sutter, Niederdorf; Ulrich Mundwiler, Tenniken, all of Switzerland

[73] Assignee: Institut Straumann AG, Waldenburg, Switzerland

[21] Appl. No.: 846,356

[22] Filed: Mar. 5, 1992

[30] Foreign Application Priority Data

Mar. 11, 1991 [CH] Switzerland .................. 720/91

[51] Int. Cl.⁵ .............................. A61B 17/56
[52] U.S. Cl. ........................ 606/72; 606/73; 606/76
[58] Field of Search .............. 606/69, 70, 71, 72, 606/73, 76, 77, 78

[56] References Cited

U.S. PATENT DOCUMENTS

| | | | |
|---|---|---|---|
| 3,905,777 | 9/1975 | Lacroix | 606/76 |
| 3,955,567 | 5/1976 | Richmond | 606/69 |
| 4,145,764 | 3/1979 | Suzuki | 606/76 |
| 4,336,617 | 6/1982 | Shikita | 606/76 |
| 4,456,005 | 6/1984 | Lichty | 606/73 |
| 4,468,200 | 8/1984 | Münch | 606/73 |
| 4,484,570 | 11/1984 | Sutter | 606/72 |
| 4,790,304 | 12/1988 | Rosenberg | 606/72 |
| 4,858,601 | 8/1989 | Glisson | 606/73 |
| 5,053,036 | 10/1991 | Perren | 606/73 |
| 5,085,660 | 2/1992 | Lin | 606/69 |

Primary Examiner—Robert A. Hafer
Assistant Examiner—Michael Brown
Attorney, Agent, or Firm—Anderson Kill Olick & Oshinsky

[57] ABSTRACT

A means for fastening a capping on bone tissue or the like over an area of original, locally depressed, chipped or fractured tissue to promote the growth of additional tissue is disclosed, comprising generally, a pin which has, at one end, a bead for attachment of a foil and, at the other end, an external thread for threading into the original tissue or bone. Between the bead and the thread is a smooth-walled segment whose diameter is preferably larger than the diameter of the external thread. The method, unlike previous prior art methods, facilitates growing of the bone between two teeth or between teeth and a denture. The method permits, for example, restoring a jawbone to a larger extent than over areas where there were only slight depressions.

22 Claims, 1 Drawing Sheet

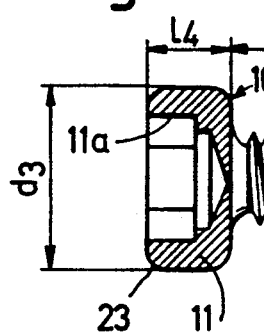
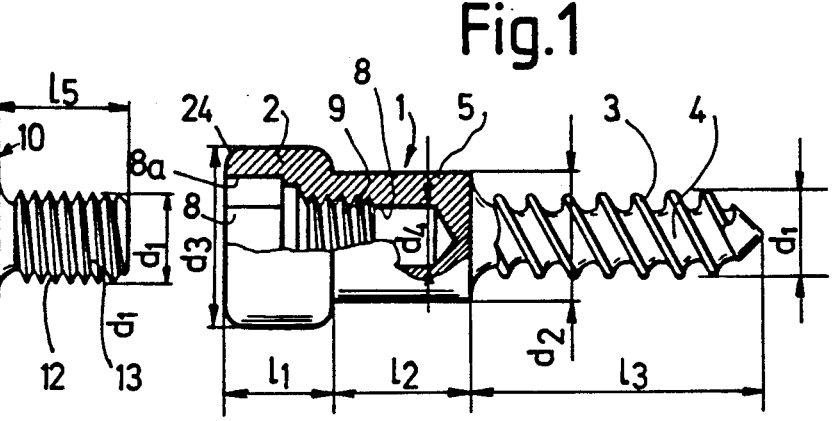
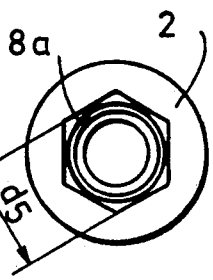
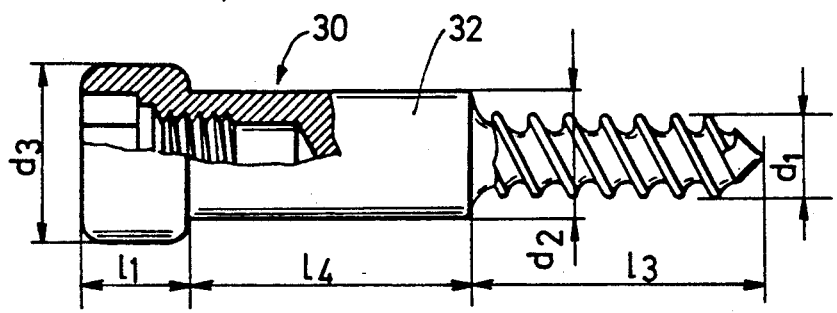
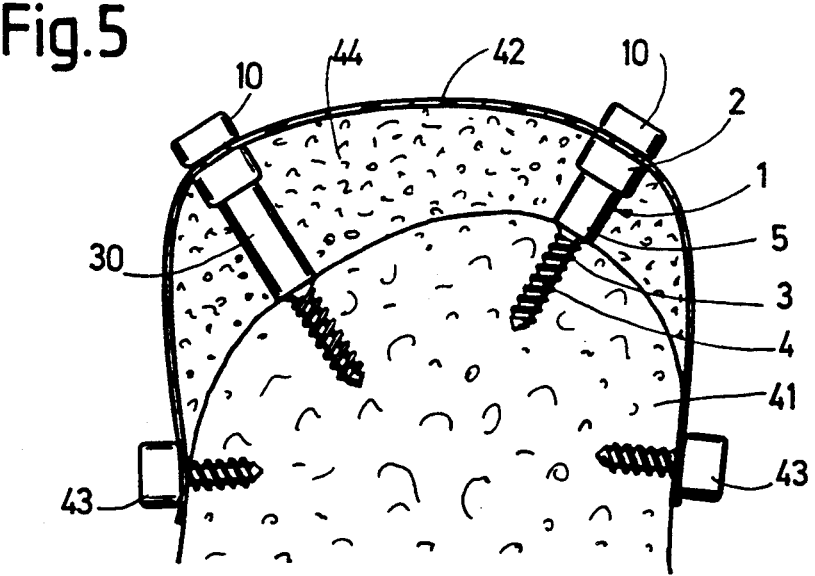

AUXILIARY MEANS AND METHOD FOR FASTENING A CAPPING ON BONE TISSUE OR THE LIKE

FIELD OF THE INVENTION

The present invention is directed to promoting the growth of tissue in localized areas and more particularly to the fastening of a capping on a bone, such as a jawbone, to promote the formation of new tissue.

BACKGROUND OF THE INVENTION

Bones, such as jawbones (e.g. the mandible), can be abraded or fractured or otherwise result in localized depressions because of diseases which, for example, effect a body's calcium content or because of infections destroying bone tissue. Such destruction or slight unevenness can be "repaired" if new bone tissue can be made to grow into the fractured or abraded areas by using, for instance, a cuff comprised of a pliable, tissue-friendly foil. The cuff would permit the formation of new bone material beneath it until the new material reaches its underside surface. Such methods, to data however, could be used for restoring only very small depressions or localized unevenness.

It is therefore an object of the invention to create an auxiliary means and method for fastening a capping on bone tissue or the like.

Another object of the invention is to provide an auxiliary means and method for fastening a capping on bone tissue to promote the formation of new bone or tissue to levels not achieved in prior art methods for fastening a capping on bone tissue, particularly on the jawbone.

An additional object of the invention is to provide an auxiliary means and method for fastening a capping on bone tissue or the like to facilitate growing of bone, for example, between two teeth or between teeth and a denture.

Yet another object of the invention is to provide an auxiliary means and method for fastening a capping on a bone tissue, wherein such means is economical and safe.

SUMMARY OF THE INVENTION

These and other objects of the invention, which will become apparent hereafter, are achieved by an auxiliary means and method for fastening a capping on bone tissue or the like, comprising generally a pin, having a bead at one end with a face for engagement of a screwdriver or other rotational tool, an internal thread, an external thread at the other end of the pin for screw insertion into the bone tissue and a cylindrical, smooth-walled segment between the bead and external thread. A corresponding cap screw is threaded into the pin's internal thread for retention of a biocompatible foil between the pin and the screw. New tissue, such as bone tissue, grows over the abraded or fractured areas until it reaches the underside of the biocompatible foil. The invention may be employed to facilitate growing of bone, for example, between two teeth or between teeth and a denture.

BRIEF DESCRIPTION OF THE DRAWINGS

The invention will be better understood in the Detailed Description of the Preferred Embodiments, in conjunction with the appended drawings, in which:

FIG. 1 is a side, partially cutout and partially perspective view of the pin according to the invention;

FIG. 2 is a partially side view and partially perspective view of a cap screw associated with the pin of FIG. 1;

FIG. 3 is a front view of the pin of FIG. 1;

FIG. 4 is a partially cutout and partially perspective view of a second embodiment of the pin; and FIG. 5 is a cross sectional view of a jawbone with pins inserted therein.

DETAILED DESCRIPTION OF THE PREFERRED EMBODIMENT

Reviewing now the drawings, wherein like numerals reflect like elements throughout the several views, FIGS. 1 and 3 depict pin 1, comprising bead 2 on its left end and segment 4, on its right end, having external thread 3 to be screwed into tissues, such as a jawbone. Thread 3 has a profile with is particularly suited for being threaded into bone. Between the external thread 3 carrying segment 4 and bead 2 is a smooth-walled cylindrical segment 5. Cylindrical segment 5 has a diameter $d_2$ which is at least as large although preferably somewhat larger than diameter $d_1$ of the external thread 3. Bead 2 contains dead end hole 8 which extends from the left side of the bead 2 and pin 1 into the pin 1.

The hole 8 has an internal hexagonal surface 8a which facilitates the insertion of a hexagonal screwdriver or similar rotational tool whose dimensions conform to existing standards. The dead end hole 8 furthermore has an internal thread 9 (extending further internally from hexagonal surface 8a) and is dimensioned to accommodate screw 10 (See FIGS. 2, 5) until screw head 11 contacts bead 2.

Screw head 11 is configured to conform to the bead 2 and has the same diameter $d_3$ which is preferably identical to the diameter of the bead 2. The diameter of threaded segment 13 is configured to allow for adequate wall thickness in the region of the internal thread 9 of the pin 1 and to accommodate external thread 12. Although various dimensions for the elements employed in the invention may be used, the following dimensions have been shown to be effective and are deemed to be preferred for a typical application, at this time:

| | | |
|---|---|---|
| $d_1 =$ | diameter of the external threads 3 at pin 1 | 1.2 mm |
| $d_2 =$ | diameter of the cylindrical segment | 51.8 mm |
| $d_3 =$ | diameter of the bead 2 on the pin 1 and the diameter of the head 11 of the screw 10 | 2.5 mm |
| $d_1 =$ | diameter of the external thread 12 of the screw 10 | 1.2 mm |
| $d_4 =$ | diameter of the portion of the dead end hole 8 which has no thread | 1 mm |
| $d_5 =$ | face spacing in the hexagonal hole 8a (see FIG. 3a) | 0.87 mm |
| $L_1 =$ | axial length of the bead 2 | 1.5 mm |
| $L_2 =$ | axial length of the cylindrical segment 4 | 2 mm |
| $L_3 =$ | axial length of the external thread 3 bearing segment 5 | 2 mm |
| $L_4 =$ | axial length of the screw head 11 (see FIG. 2) | 1.2 mm |
| $L_5 =$ | axial length of the screw 10 | 3 mm |

FIG. 4 is a partially cutout and partially perspective view of a second embodiment of the pin of the invention. The pin 30, in this embodiment, is similar in size and dimension to pin 1, except that the axial length $L_4$ of the cylindrical smooth-walled segment 32 is twice as long as the corresponding segment 5 in the first embodiment. Of course, longer or shorter segment pins may be used according to, for example, the amount of tissue which must be grown to rebuild the bone to the desired amount.

Additionally, the internal hole could be shaped for engagement of a rotational tool or screwdriver having, for instance, a triangular, square or five-cornered surface, rather than a hexagonal surface. Furthermore, two radially extending slots could be provided on the edge 24 of the pin and also on the corresponding edge 23 of the screw 10 for engagement of a conventional screwdriver.

FIG. 5 cross-sectionally depicts typical use of the invention. Two pins 1, 30 are threaded into the jawbone 41 to such a depth that the entire carrying segment 4 of each pin is located inside the bone. A tissue-friendly capping foil 42, preferably comprised of polytetrafluoroethylene, is placed over these pins and fastened at the foil edge to the jawbone with screws 43. Screws 10 are then threaded into pins 1 and 30 for subsequently securing foil 42. Experience has shown that bone mass 44 will begin to grow between the bone 41 and the foil 42 until the entire space therebetween is filled. At that time, foil 42, screws 10, 43 and pins 1, 30 may be removed to allow mucus membrane the opportunity again to grow across the bone.

While the invention has been illustrated and described as embodied in the auxiliary means for fastening a capping on bone tissue or the like, it is not intended to be limited to the details shown, since various modifications and structural changes may be made without departing in any way from the spirit of the present invention.

What is claimed is:

1. A method of securing a cover over an area of original, locally depressed, chipped, or fractured tissue to promote the growth of additional tissue, comprising the steps of:
   providing a pin having, on one end, external thread and, on another end, internal thread and a bead, wherein said bead has an engagement face for engaging a rotational tool;
   providing a cylindrical, smooth-walled segment between said bead and the external thread, wherein the diameter of said segment is greater than or equal to the diameter of the external thread;
   detachably securing said external thread into or near the original tissue;
   covering said pin and said area with a foil; and
   threading a cap screw into said internal thread of the pin, wherein said cap screw retains said foil against said bead of the pin.

2. The method of claim 1, wherein said tissue is bone.

3. The method of claim 1, wherein said engagement face is an internal square.

4. The method of claim 1, wherein said engagement face is an internal hexagonal surface.

5. The method of claim 1, wherein said cylindrical segment has an axial length of at least 2 mm.

6. The method of claim 1, wherein the length of the segment with the internal thread is 3 to 5 mm.

7. The method of claims 1, 3, 5 or 6, wherein the external thread has a diameter of 1.2 mm.

8. The method of claim 7, wherein the cylindrical segment has a diameter of 1.8 mm.

9. The method of claim 8, wherein the bead has a diameter of 2.5 mm.

10. The method of claims 1, 3, 5 or 6 wherein the diameter of the bead of the cap screw corresponds to the diameter of the bead of the pin.

11. The method of claim 1, wherein the cap screw has an engagement face for application of a screwdriver, wherein said engagement is configured identically to an engagement face which is placed at the bead for application of a screwdriver.

12. An auxiliary means for fastening a cover over an area of original, locally depressed, chipped or fractured tissue to promote the growth of additional tissue, comprising:
   a pin including:
      external thread on one of the pin; a bead on the other end;
      internal thread, within said pin, at said other end; a cylindrical, smooth-walled segment between said bead and the external thread, wherein the diameter of said segment is greater than or equal to the diameter of the external thread;
   a foil positioned over said area and over the bead of the pin; and
   a cap screw means for maintaining said foil over said area and said pin, wherein said cap screw is detachably securable to said pin.

13. The auxiliary means of claim 12, wherein said sleeve is bone.

14. The auxiliary means of claim 12, further comprising an engagement face having an internal square shape surface.

15. The auxiliary means of claim 12, further comprising an, engagement face having an internal hexagonal shape surface.

16. The auxiliary means of claim 12, wherein said cylindrical segment has an axial length of at least 2 mm.

17. The auxiliary means of claim 12, wherein the length of the segment with the internal thread is 3 to 5 mm.

18. The auxiliary means of claims 12, 14, 16, or 17, wherein the external thread has a diameter of 1.2 mm.

19. The auxiliary means of claim 18, wherein the cylindrical segment has a diameter of 1.8 mm.

20. The auxiliary means of claim 19, wherein the bead has a diameter of 2.5 mm.

21. The auxiliary means of claims 12, 14, 16 or 17, wherein the diameter of the bead of the cap screw corresponds to the diameter of the bead of the pin.

22. The auxiliary means of claim 12, wherein the cap screw has an engagement face for application of a screwdriver, wherein said engagement is configured identically to an engagement face which is placed at the bead for application of a screwdriver.

* * * * *